US012806308B2

(12) United States Patent
Kim et al.

(10) Patent No.: US 12,806,308 B2
(45) Date of Patent: Nov. 24, 2026

(54) TOPICAL HEMOSTATIC POWDER COMPOSITION AND PREPARATION METHOD THEREFOR

(71) Applicant: THERACION BIOMEDICAL CO. LTD., Seongnam-si (KR)

(72) Inventors: Eun Jin Kim, Seongnam-si (KR); Byung Nam Kim, Chungcheongbuk-do (KR)

(73) Assignee: THERACION BIOMEDICAL CO. LTD., Seongnam-si (KR)

( * ) Notice: Subject to any disclaimer, the term of this patent is extended or adjusted under 35 U.S.C. 154(b) by 522 days.

(21) Appl. No.: 18/006,061

(22) PCT Filed: May 31, 2021

(86) PCT No.: PCT/KR2021/006759
§ 371 (c)(1),
(2) Date: Jan. 19, 2023

(87) PCT Pub. No.: WO2022/019467
PCT Pub. Date: Jan. 27, 2022

(65) Prior Publication Data

US 2023/0277721 A1 Sep. 7, 2023

(30) Foreign Application Priority Data

Jul. 20, 2020 (KR) ........................ 10-2020-0089427

(51) Int. Cl.
*A61L 26/00* (2006.01)
*A61L 15/22* (2006.01)
(Continued)

(52) U.S. Cl.
CPC ......... *A61L 26/0023* (2013.01); *A61L 15/225* (2013.01); *A61L 24/00* (2013.01);
(Continued)

(58) Field of Classification Search
None
See application file for complete search history.

(56) References Cited

U.S. PATENT DOCUMENTS 4,394,373 A * 7/1983 Malette ................. A61L 31/042 623/915
2010/0092525 A1* 4/2010 Hardy ..................... A61L 15/44 514/782
2014/0023714 A1* 1/2014 Gagnieu ................... A61P 7/04 424/94.64

FOREIGN PATENT DOCUMENTS

EP 2968651 B1 * 10/2020 ......... A61L 26/0061
KR 10-2008-0030094 A 4/2008
(Continued)

OTHER PUBLICATIONS

Singh et al ("Hemostatic Comparison of a Polysaccharide Powder and a Gelatin Powder", Journal of Investigative Surgery, vol. 32(5) (2019), p. 393-401 (Year: 2019).*
(Continued)

*Primary Examiner* — Sin J Lee
(74) *Attorney, Agent, or Firm* — Sughrue Mion, PLLC

(57) ABSTRACT

A topical hemostatic powder composition and a preparation method for manufacturing the powder composition are disclosed. The powder-type hemostatic agent includes a super-absorbent polymer and a bioadhesive polymer (BP). The power-type hemostatic agent is biodegradable in vivo and superb in terms of hemostasis effectiveness, thereby suitable for various applications in surgical procedures and minimal invasive surgery such as endoscopy, laparoscopy, and the like.

16 Claims, 10 Drawing Sheets

Thiolated Chitosan Particle(TCP)

(51) Int. Cl.
*A61L 24/00* (2006.01)
*A61L 24/04* (2006.01)
*A61L 24/08* (2006.01)

(52) U.S. Cl.
CPC ........... *A61L 24/0042* (2013.01); *A61L 24/04* (2013.01); *A61L 24/043* (2013.01); *A61L 24/08* (2013.01); *A61L 26/00* (2013.01); *A61L 26/0052* (2013.01); *A61L 26/009* (2013.01); *A61L 2300/418* (2013.01); *A61L 2400/04* (2013.01)

(56) References Cited

FOREIGN PATENT DOCUMENTS

| | | | |
|---|---|---|---|
| KR | 10-2013-0055847 | A | 5/2013 |
| KR | 10-1507589 | B1 | 4/2015 |

OTHER PUBLICATIONS

Ahmed El-Mekawy et al., "Fabrication and Characterization of Fungal Chitosan-SAP Membranes for Hemostatic Application", Current Biochemical Engineering, 2014, pp. 75-82, vol. 1.
Fahanwi Asabuwa Ngwabebhoh et al., "Adsorptive removal of multi-azo dye from aqueous phase using a semi-IPN superabsorbent chitosan-starch hydrogel", Chemical Engineering Research and Design, 2016, pp. 274-288, vol. 112.
Zhengguo Wu et al., "Antibacterial and Hemostatic Thiol-Modified Chitosan-Immobilized AgNPs Composite Sponges", ACS Applied Materials & Interfaces, 2020, pp. 20307-20320, vol. 12.
Lalit Kumar Meena et al., "Study of locust bean gum reinforced cyst-chitosan and oxidized dextran based semi-IPN cryogel dressing for hemostatic application", Bioactive Materials, 2018, pp. 370-384, vol. 3.
International Search Report for PCT/KR2021/006759 dated Nov. 2, 2021.

* cited by examiner

[FIG. 1]
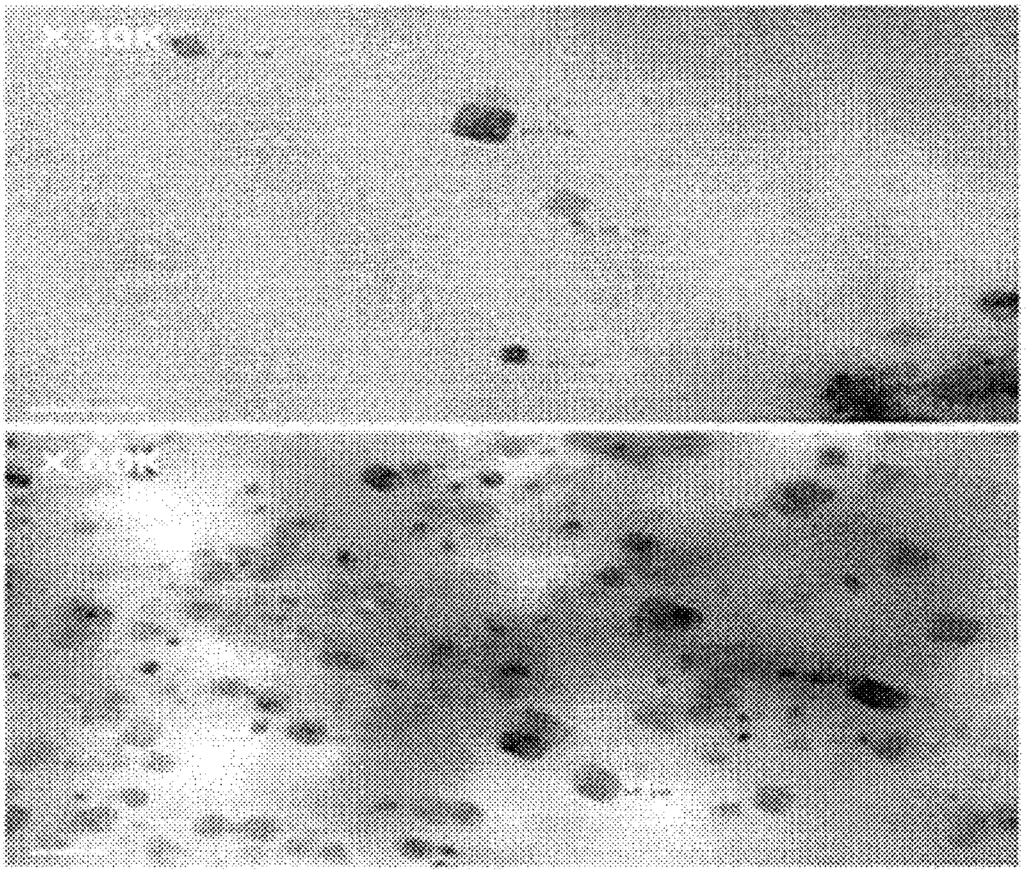
TEM (Transmission electron microscope) of Micelle(CS03) prepared

[FIG. 2]
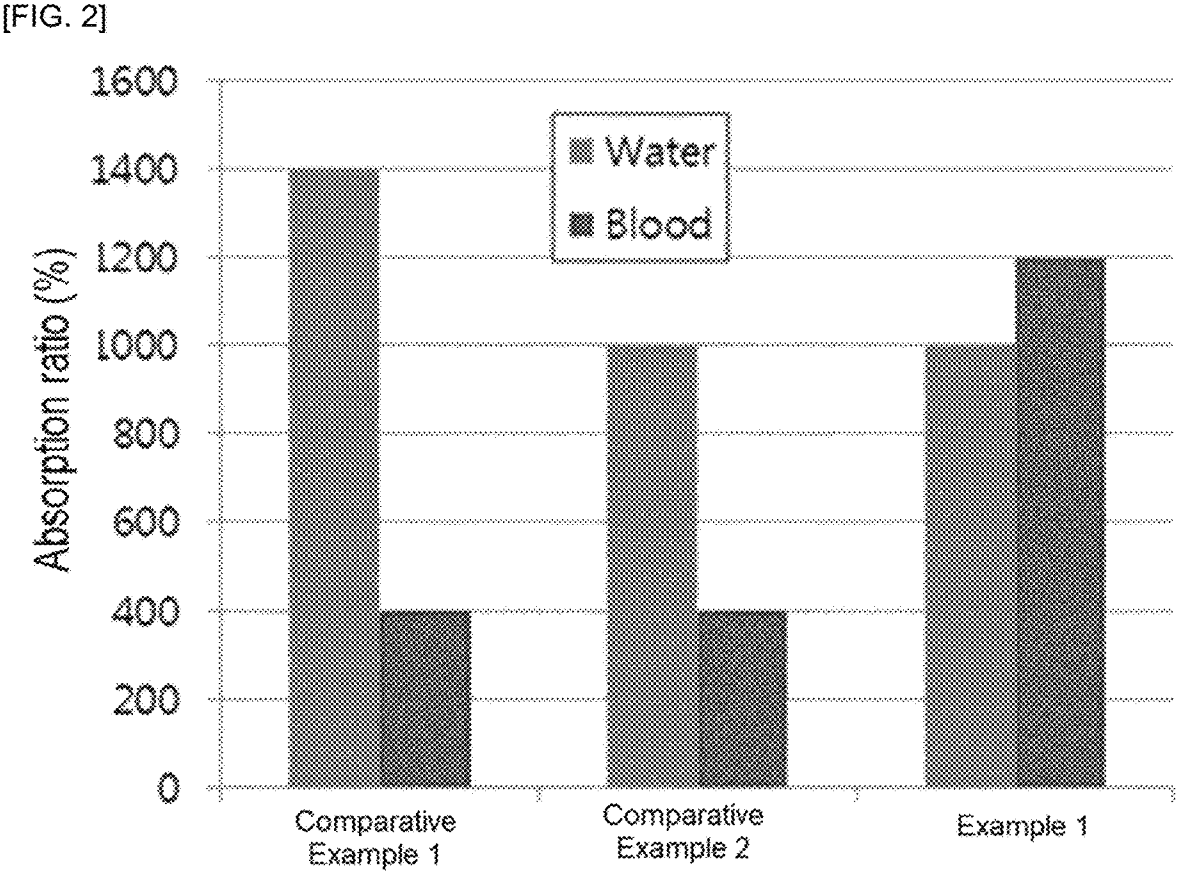

[FIG. 3]
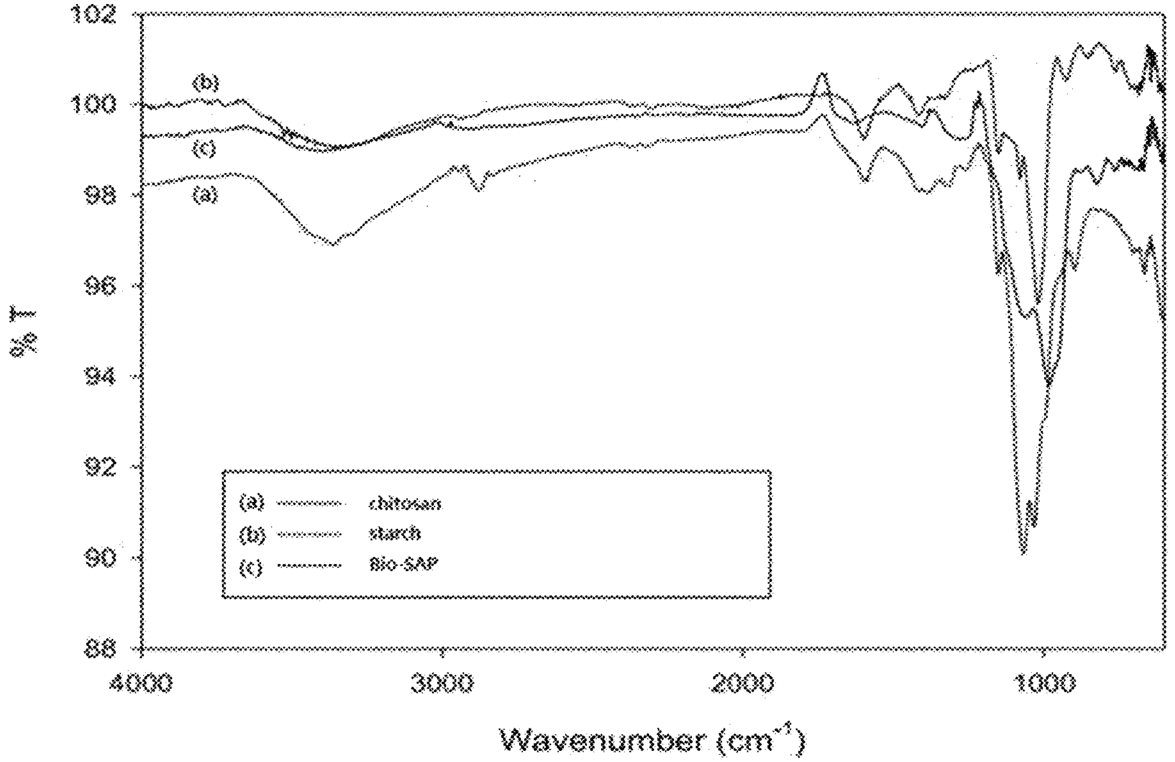
[FIG. 4]
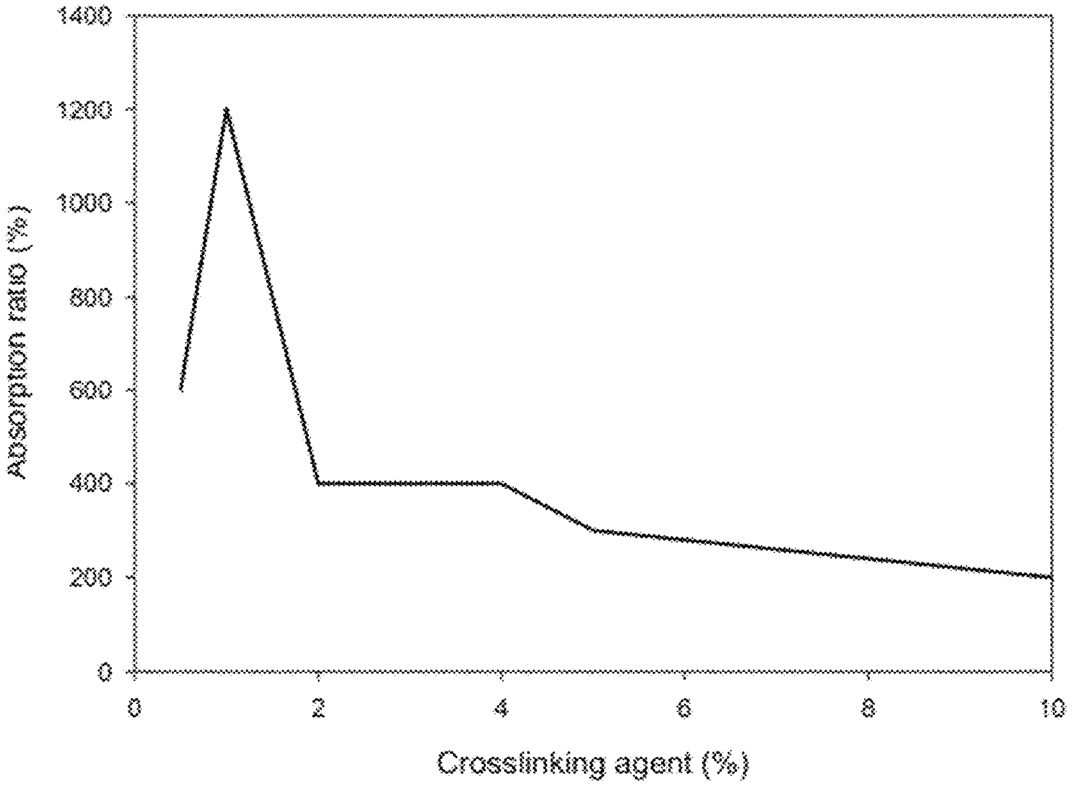

[FIG. 5]
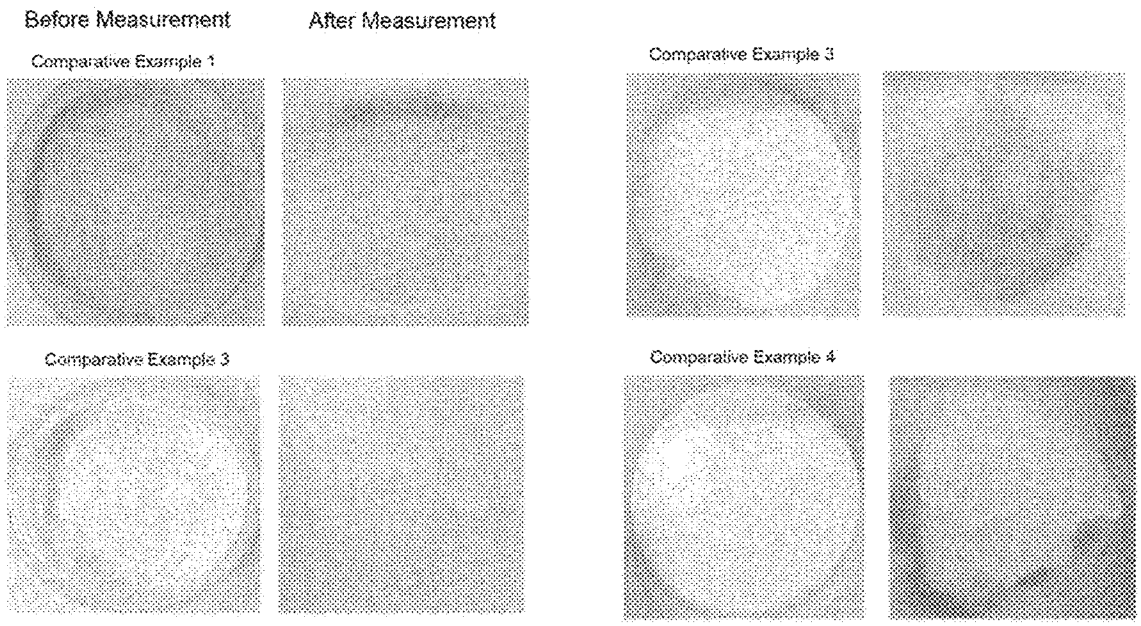
[FIG. 6]
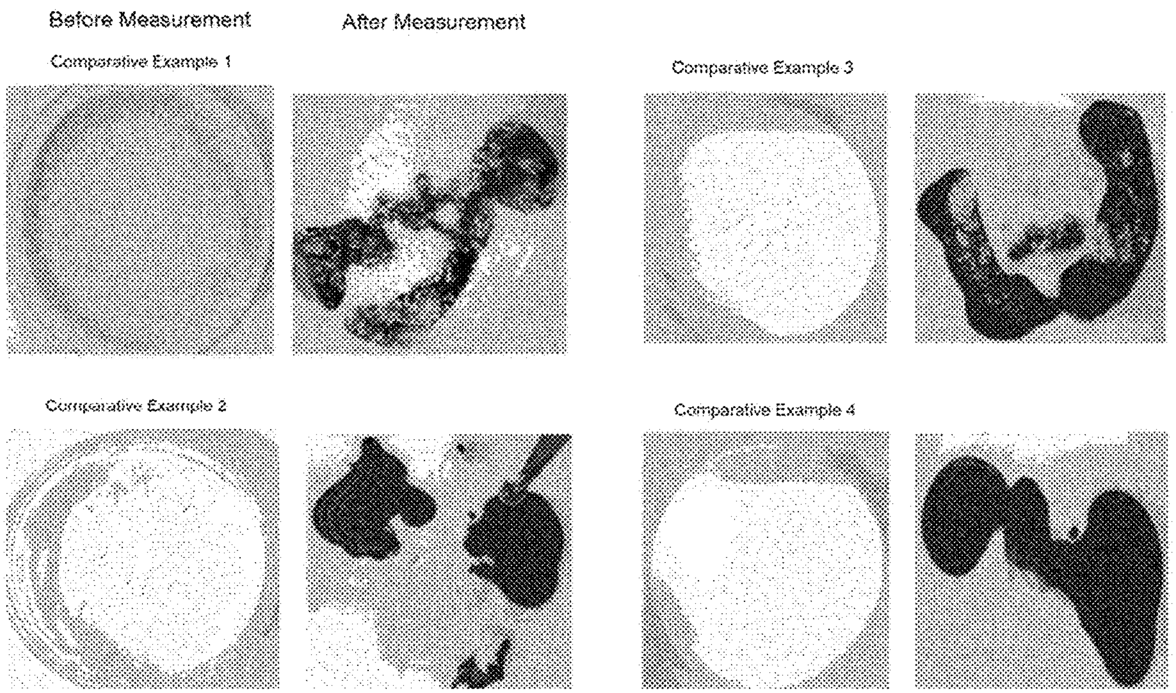

[FIG. 7]
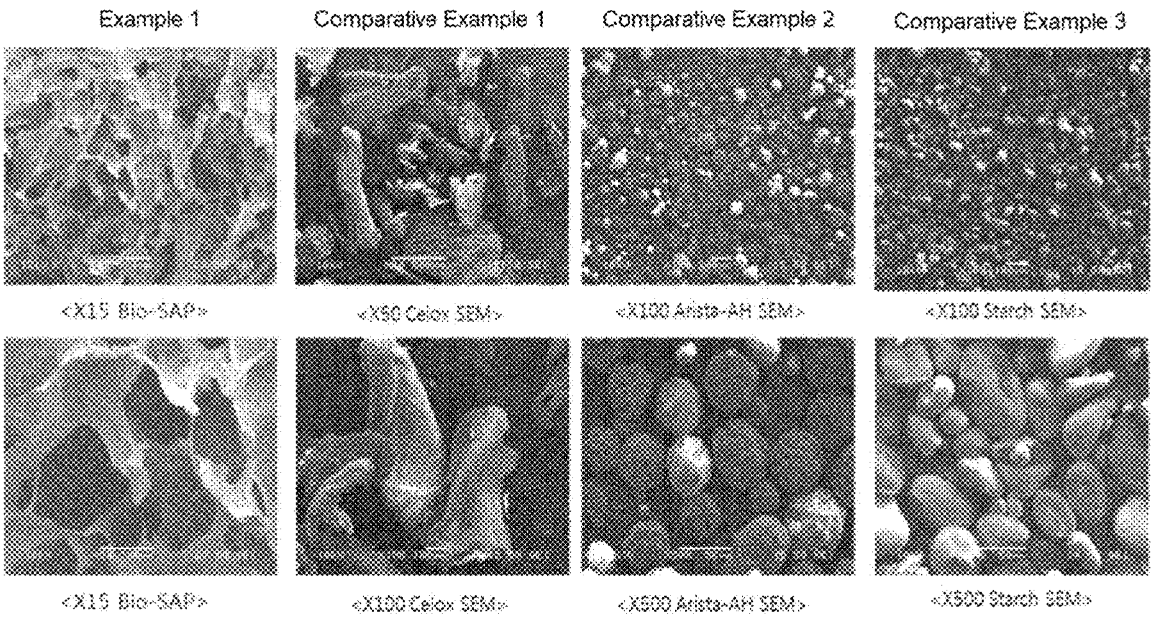
[FIG. 8]
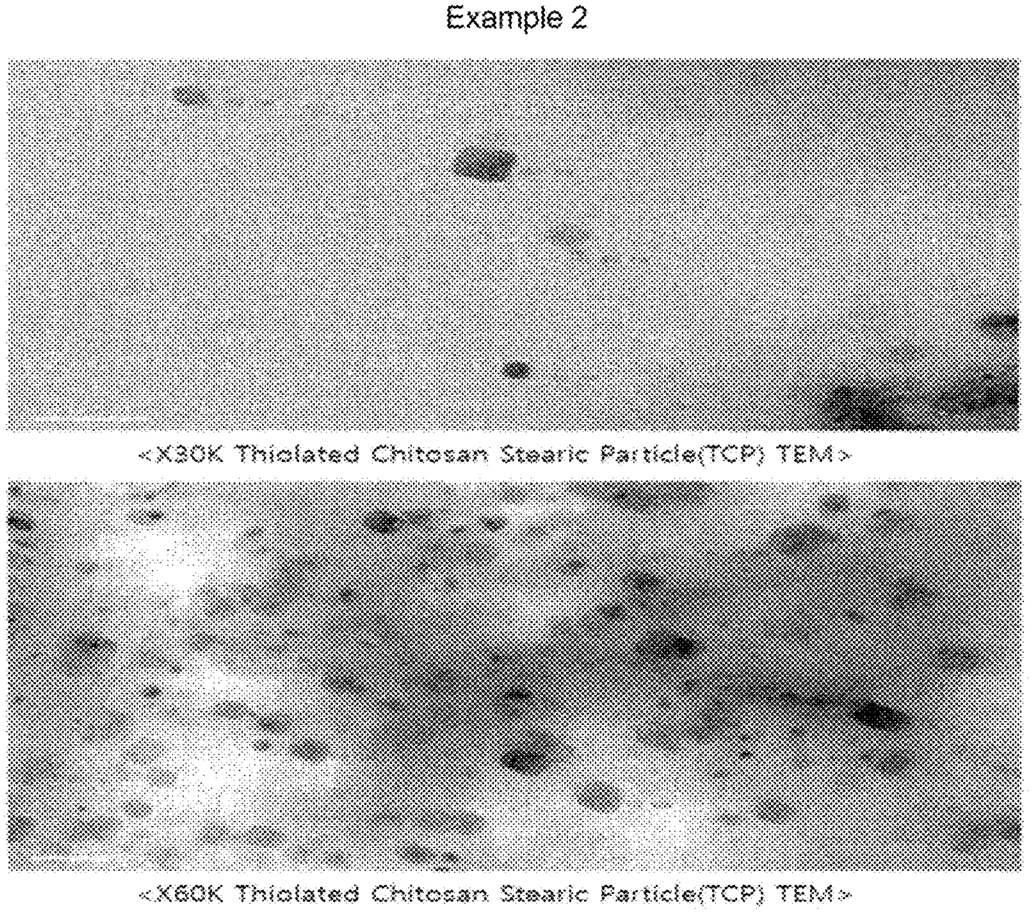

[FIG. 9]
1) Change in absorbance for TGA concentration
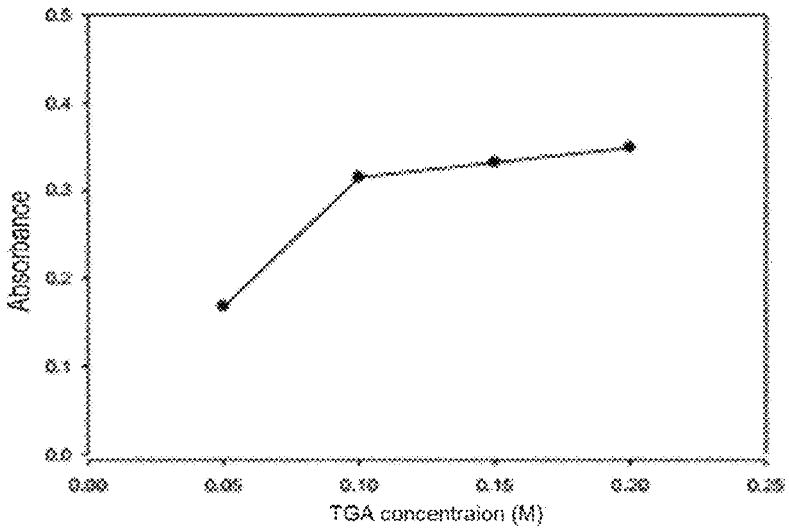
2) Change in Thiol group for TGA concentration
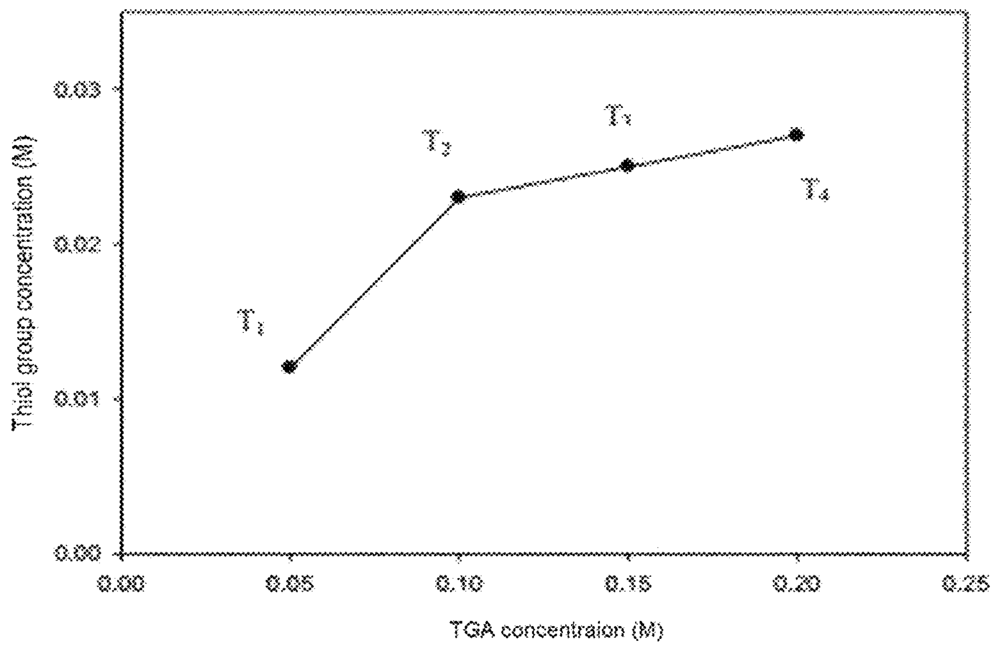
( *$T_{1,2,3,4}$ Classification number according to increase in concentration of TGA)

[FIG. 10]
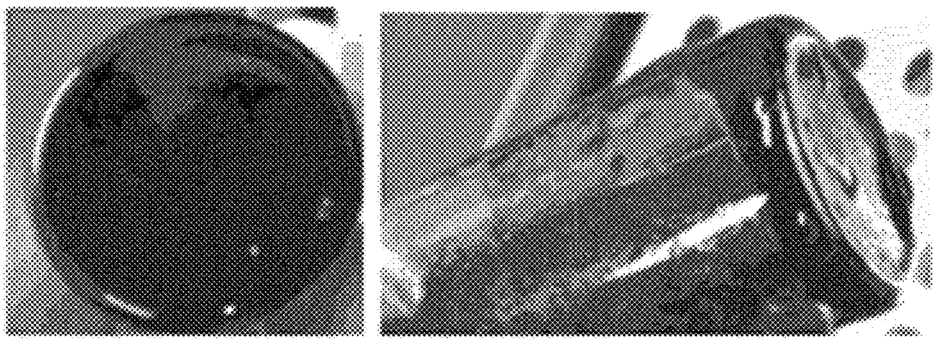
<Coagulation occurs earlier in bottom portion than overall coagulation>
[FIG. 11]
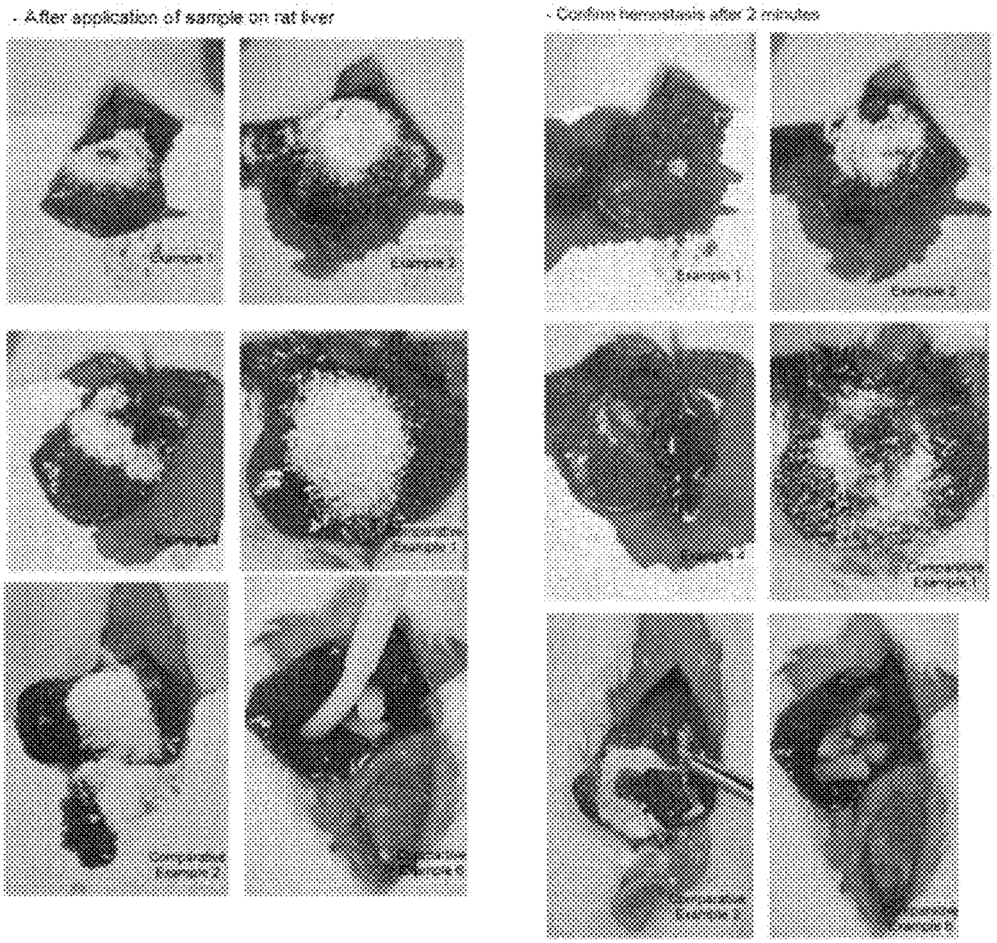

[FIG. 12]
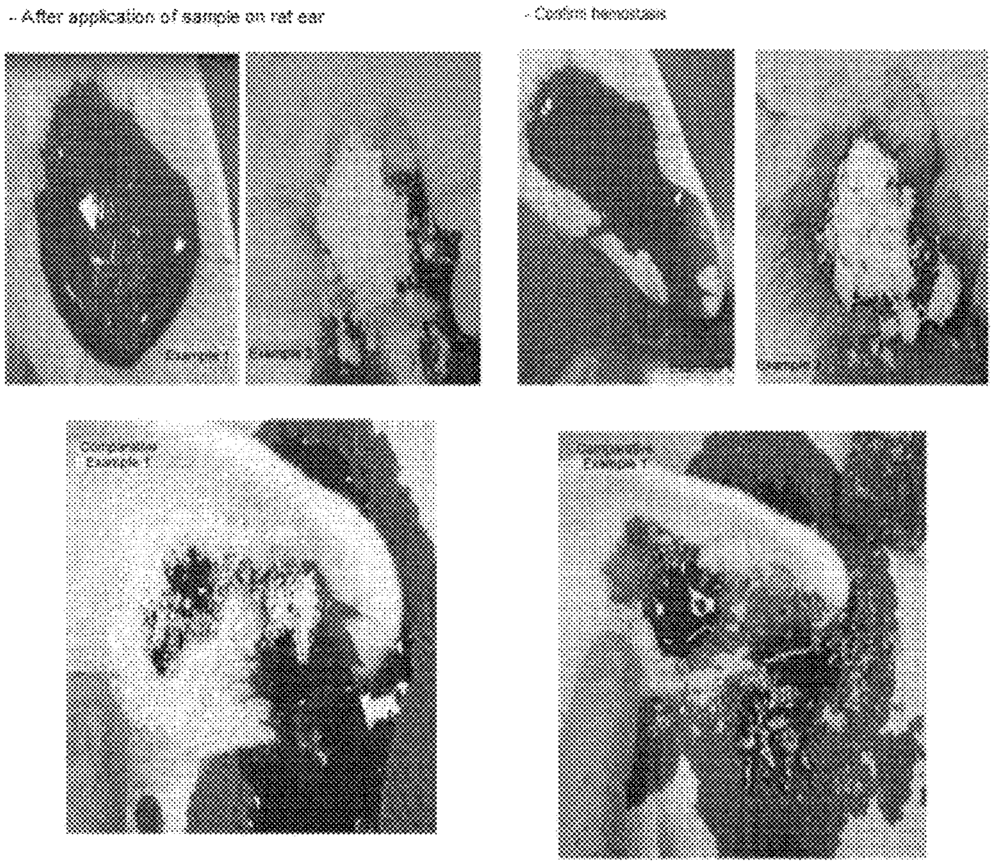

[FIG. 13]
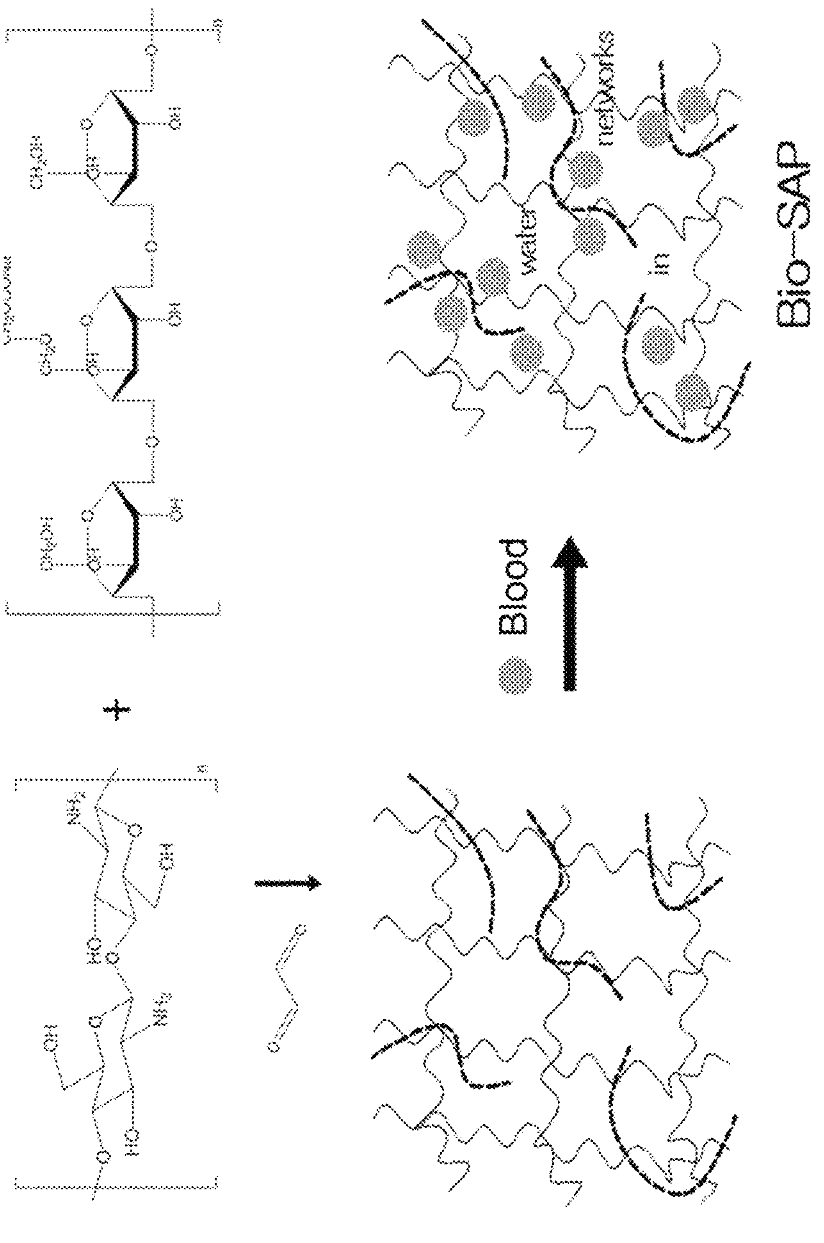

[FIG. 14]
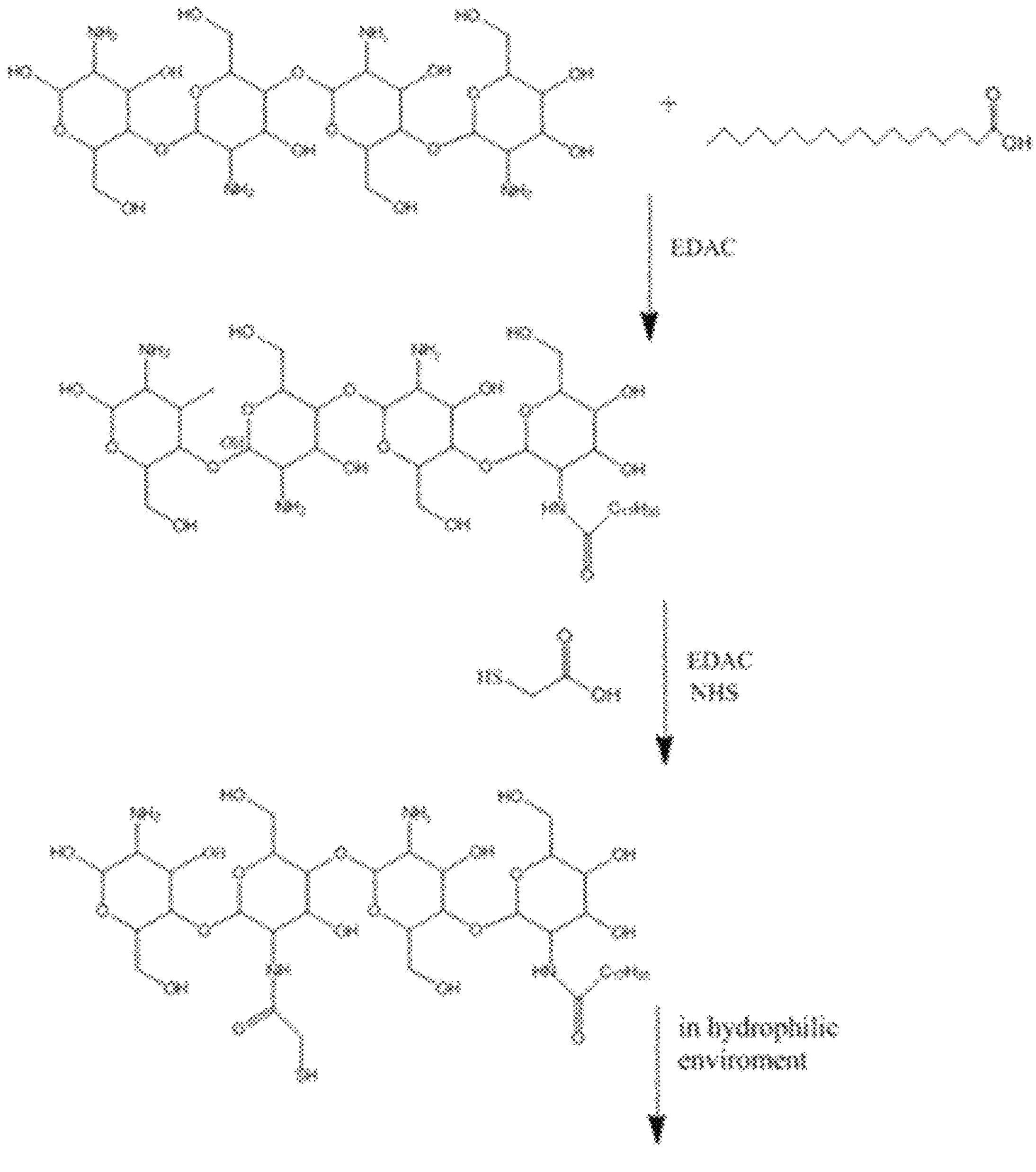
Thiolated Chitosan Particle(TCP)

TOPICAL HEMOSTATIC POWDER COMPOSITION AND PREPARATION METHOD THEREFOR

CROSS REFERENCE TO RELATED APPLICATIONS

This application is a National Stage of International Application No. PCT/KR2021/006759 filed May 31, 2021, claiming priority based on Korean Patent Application No. 10-2020-0089427 filed Jul. 20, 2020.

TECHNICAL FIELD

The present invention relates to a topical hemostatic powder composition and a preparation method therefor and, more specifically, to a technology of providing a powder-type hemostatic agent which includes a superabsorbent polymer and a bioadhesive polymer and is biodegradable in vivo and superb in terms of hemostasis effectiveness, thereby finding applications in surgical procedures and minimal invasive surgery such as endoscopy, laparoscopy, etc.

BACKGROUND ART

Blood is a body fluid that supplies oxygen and nutrients to body cells and collects and transports carbon dioxide and waste products generated by cell metabolism.

Bleeding means drainage of blood out of blood vessels. The blood vessels that make up the whole body circulate the blood in the blood vessels throughout the body by the pressure of the heart. When a wound occurs in some blood vessels, a space through which the pressure escapes is generated and blood leaks out of the wound. Bleeding, in which blood is drained out of the blood vessels, may occur in daily life injuries and medical practices such as surgery. In this case, it is of utmost importance to quickly stop bleeding from a bleeding site by suturing or compressing a wound area with a hemostatic agent, bandage, or dressing. In order to cope with this, various types of hemostatic agents using various raw materials are being developed.

For example, Korean Patent Publication No. 10-2013-0055847 discloses a hydrogel including chitosan or polyamine to which a catechol group is bonded and a polaxamer to which a thiol group is bonded to a terminal, a preparation method therefor, and a hemostatic agent using the same. More specifically, Korean Patent Publication No. 10-2013-0055847 discloses a technology related to an adhesive composition that is usable as a bioadhesive agent because it has safety inside and outside the body, is temperature-sensitive, and has excellent hemostatic effect, and a medical adhesive, an anti-adhesion agent, and a surface adsorption inhibitor including the same.

As another example, Korean Patent Registration No. 10-1507589 discloses a method for preparing a bone hemostatic agent having a composition of electrospun gelatin/biphasic calcium phosphate (BCP) and chitosan hydrogel. The method includes the steps of: (a) preparing a chitosan hydrogel layer having a porous structure; (b) preparing an electrospun gelatin/BCP mat; (c) preparing a crosslinking agent; (d) positioning the electrospun gelatin/BCP mat on the chitosan hydrogel layer and performing crosslinking with a crosslinking agent; and (e) freeze-drying a composite layer of the chitosan hydrogel layer and the electrospun gelatin/BCP. Accordingly, the technical feature is to provide an effect that can prepare a biocompatible hemostatic agent capable of providing an effective hemostatic action in case of bone bleeding and having minimal effect on bone tissue regeneration.

As described above, research into hemostatic agents has been actively conducted, but in the case of existing powder-type hemostatic agents, there is a problem in effective blood absorption or flowing with bleeding fluid, and thus, it is difficult to use them in surgical procedures.

Therefore, as a research plan to solve the above problem, the present invention has been completed to provide a powder-type hemostatic agent that has excellent blood compatibility and biocompatibility and is applicable to surgical or minimally invasive procedures in addition to conventional use.

CITATION LIST

Patent Literature (Patent Literature 1) Korean Patent Publication No. 10-2013-0055847 (2013 May 29)

(Patent Literature 2) Korean Patent Registration No. 10-1507589 (2014 Dec. 31)

DESCRIPTION OF EMBODIMENTS

Technical Problem

The present invention aims to solve the problems of the related art and the technical problems as described above.

An object of the present invention is to provide a topical hemostatic powder composition and a preparation method therefor, which provide in vivo biodegradability and provide excellent hemostatic efficacy.

An object of the present invention is to provide a powder-type hemostatic agent capable of providing ease of storage, use and handling.

Furthermore, the powder-type hemostatic agent is usable in surgical procedures and is applicable to endoscopic and laparoscopic procedures, thereby improving the usability of the technology.

Solution to Problem

According to an embodiment of the present invention, there is provided a topical hemostatic powder composition including a biodegradable superabsorbent polymer (Bio-SAP) and a bioadhesive polymer (BP).

According to an embodiment of the present invention, there is provided a topical hemostatic powder including the composition described above.

According to an embodiment of the present invention, there is provided a method for preparing a topical hemostatic powder composition, the method including the steps of: (a) preparing solutions A and B; (b) forming a biodegradable superabsorbent polymer (Bio-SAP) by adding a crosslinking agent to a mixed solution in which the solutions A and B are mixed with each other; (c) preparing a bioadhesive polymer (BP); and (d) mixing the biodegradable superabsorbent polymer (Bio-SAP) with the bioadhesive polymer (BP).

Advantageous Effects of Disclosure

The present invention may provide a topical hemostatic powder composition and a preparation method therefor.

The topical hemostatic powder composition according to the present invention may provide biodegradability in vivo and significantly improve blood absorption, thereby providing excellent hemostatic efficacy.

In addition, it is possible to solve the problem that a conventional powder-type hemostatic agent flows with bleeding fluid.

The present invention may provide a powder-type hemostatic agent capable of providing ease of storage, use and handling.

The present invention may provide a safe and inexpensive powder-type hemostatic agent which does not cause an immune response.

In addition, the powder-type hemostatic agent is usable in surgical procedures and is applicable to endoscopic and laparoscopic procedures, thereby providing an effect of improving the usability of the technology.

BRIEF DESCRIPTION OF DRAWINGS

FIG. 1 shows a transmission electron microscope (TEM) image of a bioadhesive polymer (BP) according to the present invention.

FIG. 2 shows blood and water absorption ratios according to Example 1 and Comparative Examples 1 and 2 according to the present invention.

FIG. 3 shows IR values of a biodegradable superabsorbent polymer (Bio-SAP) and raw materials thereof according to the present invention.

FIG. 4 shows a blood absorption amount according to a concentration of a crosslinking agent according to the present invention.

FIG. 5 is a result showing water absorption amounts according to Comparative Examples 1 to 4 according to the present invention.

FIG. 6 is a result showing blood absorption amounts according to Comparative Examples 1 to 4 according to the present invention.

FIG. 7 is a result showing scanning electron microscopy (SEM) images according to Example 1 and Comparative Examples 1 to 3 according to the present invention.

FIG. 8 is a result showing a TEM image of thiolated chitosan stearic particle (TCP) of Example 2 according to the present invention.

FIG. 9 is a result showing absorbance and concentration of a thiol group according to a thio glycolic acid (TGA) concentration of TCP according to the present invention.

FIG. 10 is an image of coagulation in an in vitro hemostatic ability test according to the present invention.

FIG. 11 shows in vivo hemostatic ability test images according to Examples 1, 2, and 4 and Comparative Examples 1, 2, and 6 according to the present invention.

FIG. 12 shows in vivo hemostatic ability test images according to Examples 1 and 2 and Comparative Example 1 according to the present invention.

FIG. 13 shows a Bio-SAP formation process of the present invention.

FIG. 14 shows the a TCP formation mechanism of the present invention.

MODE OF DISCLOSURE

Reference is made to the accompanying drawing which shows, by way of illustration, specific embodiments in which the present invention may be practiced. The embodiments will be described in detail in such a manner that the present invention can be carried out by those of ordinary skill in the art. It should be understood that various embodiments of the present invention are different from each other, but need not be mutually exclusive. For example, certain shapes, structures, and features described herein may be implemented in other embodiments without departing from the spirit and scope of the present invention in connection with one embodiment. In addition, it will be understood that the locations or arrangement of individual components in the disclosed embodiments can be changed without departing from the spirit and scope of the present invention. Therefore, the following detailed description is not to be taken in a limiting sense, and the scope of the present invention is to be limited only by the appended claims and the entire scope of equivalents thereof, if properly explained. Like reference numerals in the drawing refer to the same or similar functions throughout the various aspects.

Hereinafter, preferred embodiments of the present invention will be described in detail with reference to the accompanying drawing, so that those of ordinary skill in the art can easily carry out the present invention.

According to an embodiment of the present invention, there is provided a topical hemostatic powder composition including a biodegradable superabsorbent polymer (Bio-SAP) and a bioadhesive polymer (BP).

According to an embodiment of the present invention, the biodegradable superabsorbent polymer (Bbo-SAP) has a structurally crosslinked polymer structure, has the ability to absorb moisture such as a fluid including water or moisture, and can absorb up to 30 times the original volume. Therefore, it is possible to provide a topical hemostatic powder including the Bio-SAP, which has excellent blood absorption and hemostatic ability and excellent biodegradability in the body.

According to an embodiment of the present invention, the biodegradable superabsorbent polymer (Bio-SAP) may be preferably polysaccharide. The polysaccharide provided herein includes, for example, at least one selected from starch, modified starch chitosan, pullulan, keratin, alginate, carrageenan, cellulose, natural gums, hyaluronic acid, glycosaminoglycans (GAGs), and derivatives thereof.

The natural gums may be tragacanth, and the glycosaminoglycans (GAGs) may be chondroitin sulfate.

According to an embodiment of the present invention, there is provided the topical hemostatic powder composition in which the biodegradable superabsorbent polymer (Bio-SAP) has a structure of interpenetrating polymer networks (IPN) or semi interpenetrating polymer networks (SIPN) by Structural Formula 1, Structural Formula 2, and a crosslinking agent. Hereinafter, Structural Formula 1, Structural Formula 2, and the crosslinking agent will be described in more detail.

According to an embodiment of the present invention, Structural Formula 1 is as follows.

[Structural Formula 1]

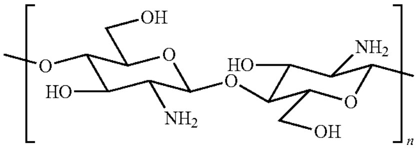

Structural Formula 1 represents the structure of chitosan. In this case, n is 155 to 3,235. In general, chitosan may have a weight average molecular weight of 50,000 to 1,100,000, but the present invention is not limited thereto.

Chitosan refers to a material obtained by deacetylating chitin. More specifically, chitin is a mucopolysaccharide with β-1,4-linked N-acetylglucosamine. Chitin is contained as a component in the shells of crustaceans such as shrimp, crab, or lobster, the epidermis of insects, and the cell walls of mushrooms or fungi. In plants, chitin is a natural polymer material that plays an auxiliary role with a support of a living organism, such as cellulose. Chitosan is a polysaccharide with β-1,4-2-amino-2-deoxy-D-glucose and is prepared by deacetylating chitin. Therefore, the molecular weight of chitosan is smaller than the molecular weight of chitin.

In addition, chitosan is soluble in aqueous organic acids and has a high viscosity. This varies depending on molecular weight, degree of deacetylation, ionic strength, pH, and the like. In addition, chitosan has excellent biocompatibility and has excellent adsorption properties by forming chelate with metal ions. Since chitosan absorbs body fluids or leachate, a hemostatic effect can be efficiently provided at a bleeding site. In particular, chitosan does not significantly affect the shape of the chelate even when ions of magnesium, copper, and potassium exist in a large amount. In addition, chitosan is a natural polymer that is less likely to be depleted, exhibits excellent biocompatibility in tissues or bodies of humans, animals, or plants, has little toxicity, and is easily biodegradable.

According to an embodiment of the present invention, Structural Formula 2 is as follows.

[Structural Formula 2]

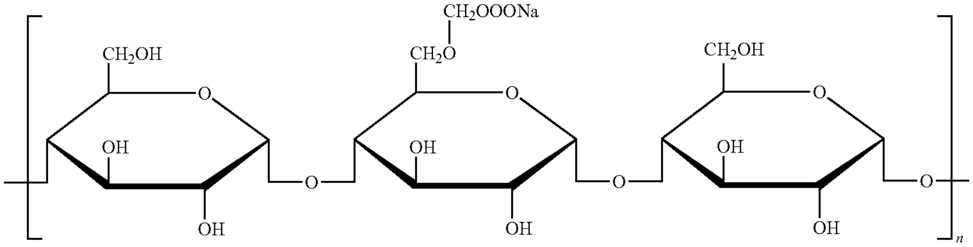

Structural Formula 2 refers to modified starch, and preferably sodium starch glycolate. In this case, n is 800 to 1,800. The sodium starch glycolate provides excellent fluidity and mixability, and provides high swelling when in contact with moisture. Typically, the sodium starch glycolate has a weight average molecular weight of 500,000 to 1,000,000.

According to an embodiment of the present invention, the crosslinking agent may include at least one selected from glyoxal, glutaraldehyde, citric acid, 1-ethyl-3(3-dimethylaminopropyl)carbodiimide (EDAC), N-hydroxysuccinimide (NHS), diisocyanate, and diacetaldehyde. Glyoxal may be preferably provided. Glyoxal is also called glyoxylaldehyde as a common name. By adding glyoxal to sodium starch glycolate, aggregation occurs through crosslinking with each other, and in the present invention, it can serve as a crosslinking agent.

Table 1 below shows result values obtained by applying glutaraldehyde, glyoxylaldehyde, and citric acid as the crosslinking agent.

TABLE 1

| | Sample weight | Absorption amount | Absorption ratio[1)] | Absorption speed[2)] |
|---|---|---|---|---|
| Bio-SAP (chitosan + starch) Glutaraldehyde 1% | 0.5 | 8 | 1600 | 1 |
| Bio-SAP (chitosan + starch) Glyoxal 1% | 0.5 | 6 | 1200 | 1 |
| Bio-SAP (chitosan + starch) Citric acid 1% | 0.5 | 4 | 800 | 1 |

[1)]Absorption ratio (W1 − W0)*100,

[2)]Absorption speed: Within 5 seconds (1), within 10 seconds (2), within 30 seconds (3), over 30 seconds (4)

In addition, referring to Table 2 below, the hemostatic ability according to the crosslinking agent was compared through an in vitro hemostasis experiment. First, 0.1 g of each sample was added to blood, and the hemostatic ability was measured in a constant-temperature water bath at 37 °C. When the time to form a blood clot was observed over time, in a case where glutaraldehyde or glyoxal was provided as the crosslinking agent, excellent hemostatic ability was exhibited unlike other materials.

TABLE 2

| | Hemostasis time |
|---|---|
| Control group | 8 minutes 35 seconds |
| Chitosan | 5 minutes 10 seconds |
| Starch | No hemostasis |
| Bio-SAP (chitosan + starch) Glutaraldehyde 1% | 2 minutes 54 seconds |
| Bio-SAP (chitosan + starch) Glyoxal 1% | 3 minutes |
| Bio-SAP (chitosan + starch) Citric acid 1% | No hemostasis |

According to an embodiment of the present invention, there is provided a topical hemostatic powder composition in which a biodegradable superabsorbent polymer (Bio-SAP) has an interpenetrating polymer network (IPN) or semi interpenetrating polymer network (SIPN) structure by Structural Formula 1, Structural Formula 2, and the crosslinking agent. Accordingly, the Bio-SAP formation process is shown in FIG. 13.

In general, the IPN structure refers to interpenetrating polymer networks, is a new type of polymer composed of two polymers in a network form, and refers to a system in which at least one type of polymer is polymerized and crosslinked in a state of not being covalently bonded with the other polymer. In addition, the SIPN structure refers to semi interpenetrating polymer networks and means that one or more polymers form a linear or branched network. This network is formed by crosslinking using a water-soluble polymer through radiation or chemical methods, or is formed by polymerization of a hydrophilic monomer using a crosslinking agent.

Referring to FIG. 13, it can be confirmed that Structural Formula 1 and glyoxal include sodium starch glycolate, which is Structural Formula 2, in chitosan crosslinking, to provide an interpenetrating polymer network (IPN) or semi interpenetrating polymer network (SIPN) structure. Accordingly, by providing a porous structure including an SIPN structure and a semi-open cell structure at random, it is possible to rapidly improve the blood absorption and remarkably improve the hemostatic effect.

According to an embodiment of the present invention, the crosslinking agent may be included in an amount of 0.01-4 parts by weight, and preferably 0.5-2 parts by weight, based on 100 parts by weight of the biodegradable superabsorbent polymer (Bio-SAP). In this case, the crosslinking agent may be at least one selected from glyoxal, glutaraldehyde, citric acid, 1-ethyl-3(3-dimethylaminopropyl)carbodiimide (EDAC), N-hydroxysuccinimide (NHS), diisocyanate, and diacetaldehyde. Preferably, the crosslinking agent may be glyoxal or glutaraldehyde.

In particular, Table 3 below and FIG. 4 show the blood absorption amount, absorption ratio, and absorption speed according to the concentration of the crosslinking agent. In view of these results, it can be confirmed that when the crosslinking agent is provided within the above concentration range, excellent performance as the hemostatic agent can be provided. In addition, in view of the IR values provided in FIG. 3, it can be confirmed that the absorption wavelengths are similar when comparing the IR values of chitosan and starch with the peak IR values of the biodegradable superabsorbent polymer (Bio-SAP) according to the present invention.

TABLE 3

| Ratio of crosslinking agent | Sample weight (g) | Absorption amount (g) | Absorption ratio (%) [1)] | Absorption speed[2)] |
|---|---|---|---|---|
| 0.5 | 0.5 | 3 | 600 | 1 |
| 1 | 0.5 | 6 | 1200 | 1 |
| 2 | 0.5 | 2 | 400 | 1 |
| 3 | 0.5 | 2 | 400 | 1 |
| 4 | 0.5 | 2 | 400 | 1 |
| 5 | 0.5 | 1.5 | 300 | 1 |
| 10 | 0.5 | 1 | 200 | 1 |

[1)] Absorption ratio (W1 − W0)*100,
[2)]Absorption speed: Within 5 seconds (1), within 10 seconds (2), within 30 seconds (3), over 30 seconds (4)

According to an embodiment of the present invention, the bioadhesive polymer (BP) may include polysaccharide. As a specific example, the bioadhesive polymer (BP) may include at least one selected from starch, chitosan, pullulan, keratin, alginate, carrageenan, cellulose, natural gums such as tragacanth, hyaluronic acid, glycosaminoglycans (GAGs), and derivatives thereof. Preferably, modified starch, pullulan, keratin, and chitosan may be provided, but the present invention is not limited thereto.

According to an embodiment of the present invention, there is provided a topical hemostatic powder composition in which a bioadhesive polymer (BP) includes Structural Formula 3 below. The bioadhesive polymer (BP) may form a particle structure. A transmission electron microscope (TEM) image of the particle structure of the bioadhesive polymer (BP) according to the present invention can be confirmed in FIG. 8.

[Structural Formula 3]

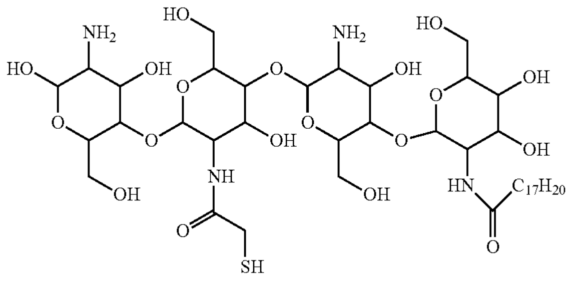

In particular, in order to improve hemostatic ability, the bioadhesive polymer (BP) according to the present invention may include at least one selected from a thiol group, a catechol group, an aldehyde group, a dihydrazide group, and a methacrylate group on the surface. Preferably, the bioadhesive polymer (BP) is provided in a chemically modified structure including a thiol group.

That is, when chitosan is provided as polysaccharide, the bioadhesive polymer (BP) structure of the present invention may be modified into thiolated chitosan stearic particle (TCP), which is a structure chemically modified by thio glycolic acid (TGA) and a crosslinking agent, so as to provide bioadhesiveness. This mechanism is shown in FIG. 14.

That is, the bioadhesive polymer (BP) may introduce a thiol group to the surface of micelle by reacting chitosan with thioglycolic acid. According to the results of FIG. 9, the change in absorbance according to the concentration of the thioglycolic acid (TGA) and the change in the concentration of the thiol group on the surface of the bioadhesive polymer can be confirmed. In addition, when the concentration of the thioglycolic acid (TGA) is in a range of 0.05 to 0.2, the thiolated chitosan stearic particle (TCP) desired in the present invention may be formed.

According to an embodiment of the present invention, there is provided a topical hemostatic powder composition in which the ratio of the biodegradable superabsorbent polymer (Bio-SAP) to the bioadhesive polymer (BP) is 2 to 8:8 to 2. Preferably, 5:5 is provided. In view of the results of Table 5 to be described below, it can be confirmed that when the ratio of the biodegradable superabsorbent polymer (Bio-SAP) to the bioadhesive polymer (BP) is within the above range, excellent performance can be provided in terms of blood absorption amount, absorption ratio, and absorption speed.

According to an embodiment of the present invention, there may be provided a hemostatic powder including the topical hemostatic powder composition. In addition, in this case, the average diameter of the powder is 1-500 μm. In addition, due to the provision in powder form, it can provide ease of handling and storage. In addition, adhesion may be improved by providing a structure that has excellent blood absorption ability and includes the biodegradable superabsorbent polymer (Bio-SAP) and the bioadhesive polymer (BP). Therefore, it is possible to compensate for a disadvantage of an existing powder that easily flows with bleeding fluid, and to provide an advantage in that the risk of retransfusion due to thrombosis is low. Furthermore, this provides an advantage in application in surgical procedures such as laparoscopic or endoscopic procedures.

On the other hand, according to an embodiment of the present invention, there is provided a method for preparing the topical hemostatic powder composition described above. In addition, the same description as the topical hemostatic powder composition describe above may be applied, and a redundant description thereof will be omitted.

According to an embodiment of the present invention, there is provided a method for preparing a topical hemostatic powder composition, the method including the steps of: (a) preparing solutions A and B; (b) forming a biodegradable superabsorbent polymer (Bio-SAP) by adding a crosslinking agent to a mixed solution in which solutions A and B are mixed with each other; (c) preparing a bioadhesive polymer (BP); and (d) mixing the biodegradable superabsorbent polymer (Bio-SAP) with the bioadhesive polymer (BP).

First, in the steps (a) and (b), the method for preparing the biodegradable superabsorbent polymer (Bio-SAP) is provided.

The solution A in the step (a) is prepared by including 1-20 parts by weight of at least one selected from starch, chitosan, pullulan, keratin, alginate, carrageenan, cellulose, natural gums, hyaluronic acid, glycosaminoglycans (GAGs), and derivatives thereof, based on 100 parts by weight of an aqueous acid solution.

For example, chitosan dissolves well in the aqueous acid solution, which is an organic solvent. The solution A is prepared by dissolving chitosan in 1-5 wt % of acetic acid. If necessary, a process of removing impurities through filtration after the dissolution and storing at room temperature may be further included.

According to an embodiment of the present invention, the solution B in the step (a) is prepared by dissolving 1-10 parts by weight of starch or modified starch based on 100 parts by weight of distilled water. Preferably, sodium starch glycolate is provided as the modified starch, and thus, excellent fluidity and mixability may be provided and high swelling may be provided when in contact with moisture. In addition, the weight average molecular weight of sodium starch glycolate is 500,000 to 1,000,000, and the dissolution temperature is 70 °C to 100 °C, and preferably 80 °C According to an embodiment of the present invention, the crosslinking agent is included in an amount of 0.01-4 parts by weight based on 100 parts by weight of the mixed solution in the step (b). Preferably, 1-2 parts by weight may be provided. When the crosslinking agent is added in the above range, gelation occurs. It can be confirmed that this is lyophilized to provide interpenetrating polymer networks (IPN) or semi interpenetrating polymer networks (SIPN) that provide excellent performance, and excellent performance as the hemostatic powder is provided.

According to an embodiment of the present invention, the crosslinking agent may include at least one selected from glyoxal, glutaraldehyde, citric acid, 1-ethyl-3(3-dimethylaminopropyl)carbodiimide (EDAC), N-hydroxysuccinimide (NHS), diisocyanate, and diacetaldehyde. Glyoxal may be preferably provided In addition, until gelation is formed by adding the crosslinking agent, the reaction conditions are that the reaction temperature is 70-100 °C and the reaction time is 3-7 hours. Preferably, the reaction temperature is 80 °C and the reaction time is 5 hours. The solution on which gelation has been performed is spray-dried to finally form a biodegradable superabsorbent polymer.

The spray drying may be performed by using a conventional spray drying apparatus, for example, a spray dryer including a drying chamber and an atomiser. The spray dryer is controlled so that the maximum drying temperature in the drying chamber does not exceed 80 °C by evaporation heat of 20-40 kg/hr. A raw material supplied to the drying chamber may be diffused and dried by the atomiser rotating at a speed of 5,000-30,000 rpm, and may be dried over the drying residence time of 10-100 seconds.

Next, in the step (c), a step of preparing the bioadhesive polymer (BP) is provided.

According to an embodiment of the present invention, the bioadhesive polymer (BP) is prepared by including 0.01-4 parts by weight of thioglycolic acid and 1-20 parts by weight of at least one selected from chitosan, collagen, hyaluronic acid, alginate, carboxymethyl cellulose, and hydroxyethyl cellulose based on 100 parts by weight of an aqueous acid solution.

In this case, the aqueous acid solution provided herein may be at least one selected from stearic acid, acetic acid, formic acid, ascorbic acid, citric acid, and oxalic acid, but the present invention is not limited thereto.

In addition, the aqueous acid solution is provided by including at least one selected from glyoxal, glutaraldehyde, citric acid, 1-ethyl-3(3-dimethylaminopropyl)carbodiimide (EDAC), N-hydroxysuccinimide (NHS), diisocyanate, and diacetaldehyde as the crosslinking agent. In this case, the crosslinking agent is included in an amount of 0.01-4 parts by weight based on 100 parts by weight of the aqueous acid solution.

When the cross-linking agent is, for example, EDAC, it refers to a water-soluble carbodiimide that may be used to crosslink biomaterials containing carboxylate acid and primary amine. Therefore, an amine group of chitosan and a carboxylic acid group of stearic acid may react to provide crosslinking. In addition, NHS refers to N-hydroxyl succinimide and may act as a coupling crosslinking agent together with EDAC to a biocompatible and biodegradable composition.

According to an embodiment of the present invention, the carboxyl group of the thioglycolic acid (TGA) may also be bonded with the primary amine of chitosan. As the concentration of the TGA increases, thiol groups increase on the surfaces of the produced micelles. Results thereof are shown in FIG. 9.

Finally, in the step (d), a step of mixing the biodegradable superabsorbent polymer (Bio-SAP) and the bioadhesive polymer (BP) is provided. In this case, in the mixing step, a mixing ratio is 2 to 8:8 to 2. The numerical meaning of the mixing ratio is the same as described above.

Hereinafter, the present invention will be described by way of examples, and the present invention is not limited thereto.

EXAMPLES

Example 1: Preparation of Bio-SAP

Solution A was prepared by dissolving 1.25 g of chitosan in 2% aqueous acetic acid solution. Solution B was prepared by adding 0.75 g of starch to distilled water and dissolving the starch at 80 °C. After mixing and stirring the solutions A and B together, a crosslinking agent (glyoxal) was added thereto to form gelation, and lyophilization was performed thereon to obtain a sample. In this case, Bio-SAP was prepared by maximally performing a reaction at a temperature of 80 °C for about 5 hours. A scanning electron microscopy (SEM) image thereof is shown in FIG. 7 together with a comparative example.

Example 2: Preparation of Mucoadhesive Polymer

Solution C was prepared by dissolving 1.25 g of chitosan in an aqueous solution of stearic acid and adding 0.05 g of EDAC as a crosslinking agent. 1.1 g of thioglycolic acid (TGA) was added to solution C, and 0.08 g of EDAC and 0.1 g of NHS were added as the crosslinking agent. Accordingly, thiolated chitosan particle (TCP) was prepared as a powder. TEM images thereof are shown in FIG. 1.

Example 3

A topical hemostatic powder was prepared by mixing Bio-SAP and BP prepared according to Examples 1 and 2. At this time, the mixing ratio is Bio-SAP:BP=2:8.

Example 4

Example 4 was prepared in the same manner as in Example 3, except that the mixing ratio was Bio-SAP:BP=5:5.

Example 5

Example 5 was prepared in the same manner as in Example 3, except that the mixing ratio was Bio-SAP:BP=8:2.

COMPARATIVE EXAMPLES

Comparative Example 1

Celox, a trademark of a commercially available hemostatic powder from Celox Media, USA, was used.

Comparative Example 2

Arista-AH, a trademark of a commercially available hemostatic powder from C.R Bard, USA, was used.

Comparative Example 3

A chitosan powder was used.

Comparative Example 4

Sodium starch glycolate was used.

Comparative Example 5

As crosslinking-chitosan, a powder in which only chitosan was crosslinked was used.

Comparative Example 6

Floseal, a trademark of a commercially available hemostatic agent from Baxter, USA, was used.

EXPERIMENTAL EXAMPLES

<Experimental Example 1: Measurement of Water Absorption Amount/Blood Absorption Amount The blood and water absorption ratios according to Example 1 and Comparative Examples 1 and 2 are shown in FIG. 2. The measurement method is the same as described below.

In addition, 0.5 g of each of Examples 1 to 5 and Comparative Examples 1 to 5 is weighed in a weight dish. 1 ml of water/1 ml of blood is sprayed to the experimental group by using a micropipette. When the dish is tilted, if water/blood flows out, it is determined that it is no longer absorbed, and the water absorption amount/blood absorption amount are recorded. The result values for the water absorption amount are shown in Table 4 and FIG. 5, and the result values for the blood absorption amount are shown in Table 5 and FIG. 6.

TABLE 4

| | Sample weight (g) | Absorption amount (g) | Absorption ratio (%)[1)] | Absorption speed[2)] |
|---|---|---|---|---|
| Comparative Example 1 | 0.5 | 7 | 1,400 | 1 |
| Comparative Example 2 | 0.1 | 1 | 1,000 | 1 |
| Comparative Example 3 | 0.5 | 3 | 600 | 1 |
| Comparative Example 4 | 0.5 | 12 | 2,400 | 1 |
| Comparative Example 5 | 0.1 | — | — | — |
| Example 1 | 0.5 | 5 | 1,000 | 1 |
| Example 2 | 0.5 | 0.5 | 100 | 2 |
| Example 3 | 0.1 | 0.9 | 900 | 2 |
| Example 4 | 0.1 | 0.6 | 600 | 2 |
| Example 5 | 0.1 | 0.4 | 400 | 2 |

[1)]Absorption ratio (W1 − W0)*100,
[2)]Absorption speed: Within 5 seconds (1), within 10 seconds (2), within 30 seconds (3), over 30 seconds (4)

TABLE 5

| | Sample weight (g) | Absorption amount (g) | Absorption ratio (%)[1)] | Absorption speed[2)] |
|---|---|---|---|---|
| Comparative Example 1 | 0.5 | 2 | 400 | 4 |
| Comparative Example 2 | 0.1 | 0.4 | 400 | 4 |
| Comparative Example 3 | 0.5 | 1 | 200 | 4 |
| Comparative Example 4 | 0.5 | 3 | 600 | 4 |
| Comparative Example 5 | 0.1 | 0.6 | 600 | 2 |
| Example 1 | 0.5 | 6 | 1,200 | 1 |
| Example 2 | 0.5 | 0.5 | 100 | 2 |
| Example 3 | 0.1 | 1 | 1,000 | 2 |
| Example 4 | 0.1 | 0.6 | 600 | 2 |
| Example 5 | 0.1 | 0.4 | 400 | 2 |

[1)]Absorption ratio (W1 − W0)*100,
[2)]Absorption speed: Within 5 seconds (1), within 10 seconds (2), within 30 seconds (3), over 30 seconds (4)

Referring to the results of FIG. 2, it can be confirmed that the blood absorption ratio in Example 1 is excellent, compared to Comparative Examples 1 and 2.

In addition, in view of Table 4 and FIG. 5 showing the water absorption amount, Comparative Examples 1 and 2 showed a water absorption amount of about 1,000%, and Comparative Example 5 showed that absorption did not occur and it was separated on the surface. In addition, compared to the case of Example 2 in which only BP (thiolated chitosan particle) was used, the improvement in water absorption ability was visually confirmed in Examples 3 to 5 in which SAP of Example 1 was mixed.

In addition, in view of Table 5 and FIG. 6 showing the blood absorption amount, compared to Example 2 in which only BP (thiolated chitosan particle) was used, the improvement in blood absorption ability was confirmed in Examples 3 to 5 in which SAP of Example 1 was mixed.

In addition, compared to the comparative example, the improvement in absorption speed can be confirmed in Examples 3 to 5. On the other hand, in the case of the comparative example of FIG. 6, it can be visually confirmed that blood is not well absorbed.

<Experimental Example 2> Quantification of Thiol Group

When synthesizing thiolated chitosan particle (TCP) prepared in Example 2, the synthesis is performed by varying the concentration of thio glycolic acid (TGA). ($T_{1,2,3,4}$: As the number increases, a higher TGA concentration is added.) After completion of the synthesis, L-Cystein is dissolved in different concentrations by using Ellman's reagent buffer solution. After measuring a calibration curve using UV, $T_{1,2,3,4}$ is also dissolved in a buffer solution in sequence, and then the absorbance is measured to calculate a concentration of a thiol group. Result values are shown in FIG. 9.

FIG. 9 shows the result values representing the absorbance and the concentration of the thiol group according to the TGA concentration. Therefore, it can be confirmed that the thiol concentration on the chitosan surface increases as the TGA concentration increases. As the concentration of thiol group increases, the adhesion to the tissue of the bleeding area increases. This shows a faster hemostatic effect because the topical hemostatic powder can be expected to interact with blood in the bleeding area and act as a physical barrier.

<Experimental Example 3> In Vitro Hemostatic Ability Test 4 ml of blood and 0.4 ul of 0.25 M $CaCl_2$) solution are added to 20 ml vial. About 0.4 ml of a sample is taken, put in the vial of 1), and then put in a constant-temperature water bath at 37 °C, and the time is measured. The time at which blood stops flowing when the vial is tilted is recorded. Result values thereof are shown in. FIGS. 6 and 10.

TABLE 6

| | Hemostasis time |
|---|---|
| Comparative Example 1 | 6 minutes 33 seconds |
| Comparative Example 2 | 7 minutes 27 seconds |
| Comparative Example 3 | 5 minutes 17 seconds |
| Comparative Example 4 | — |
| Example 1 | 3 minutes |
| Example 2 | 4 minutes 55 seconds |
| Example 3 | 3 minutes 58 seconds |
| Example 4 | 3 minutes 5 seconds |
| Example 5 | 3 minutes 30 seconds |

In view of Table 6 and FIG. 10, it can be confirmed that the hemostasis time is significantly shortened in Examples 3 to 5 according to the present invention, compared to Comparative Examples 1 to 4. In particular, it can be confirmed that the hemostasis time is greatly shortened in Example 4 in which the mixing ratio is Bio-SAP:BP=5:5. Therefore, the hemostatic powder makes it possible to secure the doctor's field of view during surgery and provide an effect of shortening the operation time. In addition, in FIG. 10, it is confirmed that coagulation occurs earlier in the bottom portion than overall coagulation.

<Experimental Example 4> In Vivo Hemostatic Ability Test (Rat Liver)

After anesthetizing the rat and incising the abdomen, the liver of the rat is taken out and fixed with a filter paper so as not to get rolled up. After incising the liver to about 1 cm, if bleeding is observed, samples are applied. The samples are applied by 0.4 ml. Since it was not clear to distinguish the time at which bleeding no longer occurred, the hemostatic ability was confirmed based on a time of 2 minutes. (In this case, the hemostasis time, adhesion to tissue, rebleeding, etc. are checked.)

TABLE 7

| | Hemostasis time | |
|---|---|---|
| Comparative Example 1 | 2 minutes | 2 minutes |
| Comparative Example 2 | 2 minutes (rebleeding observed) | 2 minutes |
| Comparative Example 6 | 1 minute | 2 minutes |
| Example 1 | No hemostasis | No hemostasis |
| Example 2 | 2 minutes (rebleeding observed) | Hemostasis after 2 minutes (rebleeding observed) |
| Example 3 | 2 minutes | 2 minutes (rebleeding observed) |
| Example 4 | 2 minutes | 2 minutes |
| Example 5 | 2 minutes | 2 minutes (rebleeding observed) |

In view of Table 7 above, in the case of Examples 2 to 4, it can be confirmed that the hemostatic ability is excellent. In particular, in the case of Example 4, it was confirmed that excellent hemostatic ability could be provided in that the hemostasis time was as very excellent as 2 minutes and rebleeding was not observed.

<Experimental Example 5> In Vivo Hemostatic Ability Test (Rat Ear)

After anesthetizing the rat, one ear of the rat is fixed. An incision is made in the blood vessel part about 5 cm away from the tip of the ear. If bleeding is confirmed, 0.8 ml of the experimental groups is applied. The hemostasis time is recorded. (In this case, the hemostasis time, adhesion to tissue, rebleeding, etc. are checked.)

TABLE 8

| | Average hemostasis time |
|---|---|
| Comparative Example 1 | No hemostasis |
| Example 1 | No hemostasis |
| Example 2 | 2 minutes 15 seconds |
| Example 3 | 1 minute 11 seconds |
| Example 4 | 38 seconds |
| Example 5 | 1 minute 37 seconds |

In view of Table 8, compared to Comparative Example 1, excellent hemostatic ability was confirmed in Examples 3 to 5, and it was confirmed that the average hemostasis time could also be greatly shortened in Example 4.

As a result of experimenting Examples according to the present invention with various experimental methods, it can be confirmed that the hemostatic ability, which is an essential condition of the hemostatic agent, is excellent. In the case of the hemostatic agent provided to stop or prevent bleeding during a surgical operation, effective hemostasis is important, and in particular, the time required for hemostasis is very important. Therefore, since the topical hemostatic powder according to the present invention can help manage bleeding by immediately inducing hemostasis, can secure the field of view of doctors, can enable quick surgery, and can quickly stop excessive bleeding, it can be confirmed that the topical hemostatic powder according to the present invention provides an excellent effect as the hemostatic agent.

In addition, since the topical hemostatic powder according to the present invention is a powder type, it is easy to use and has excellent hemostatic ability. Therefore, it can be applied in procedures such as laparoscopy and endoscopy. Furthermore, since it has excellent biodegradability, is harmless to the human body, does not cause an immune response, and does not cause an exothermic reaction, it can be variously applied depending on the purpose.

In addition, compared to conventional powders, it is possible to provide a safe and economically useful hemostatic agent by solving the problem of flowing well by blood.

Although the embodiments of the present invention have been described with reference to the accompanying drawings, those of ordinary skill in the art to which the present invention pertains will understand that the present invention may be embodied in other specific forms without changing the technical spirit or essential features thereof. Therefore, it should be understood that the embodiments described above are illustrative in all aspects and are not restrictive.

Therefore, it will be understood that the spirit of the present invention should not be limited to the above-described embodiments and the claims and all equivalent modifications fall within the scope of the present invention.

INDUSTRIAL APPLICABILITY

The present invention may provide a topical hemostatic powder composition and a preparation method therefor.

The topical hemostatic powder composition according to the present invention may provide biodegradability in vivo and significantly improve blood absorption, thereby providing excellent hemostatic efficacy.

In addition, it is possible to solve the problem that a conventional powder-type hemostatic agent flows with bleeding fluid.

The present invention may provide a powder-type hemostatic agent capable of providing ease of storage, use and handling.

The present invention may provide a safe and inexpensive powder-type hemostatic agent which does not cause an immune response.

In addition, the powder-type hemostatic agent is usable in surgical procedures and is applicable to endoscopic and laparoscopic procedures, thereby providing an effect of improving the usability of the technology.

The invention claimed is:

1. A topical hemostatic powder composition comprising a biodegradable superabsorbent polymer (Bio-SAP) and a bioadhesive polymer (BP), wherein the bioadhesive polymer (BP) comprises one or more selected from the group consisting of starch, chitosan chemically modified by thioglycolic acid (TGA), pullulan, keratin, alginate, carrageenan, cellulose, natural gums, hyaluronic acid, glycoaminoglycans (GAGs), and derivatives thereof, and the biodegradable superabsorbent polymer (Bio-SAP) is a chitosan-sodium starch glycolate semi interpenetrating polymer network (SIPN) structure formed by glyoxal.

2. The topical hemostatic powder composition of claim 1, wherein the bioadhesive polymer (BP) is thiolated chitosan stearic particles (TCP) that are prepared by modifying chitosan with stearic acid and thioglycolic acid (TGA) to form micelle particles.

3. The topical hemostatic powder composition of claim 2, wherein a weight ratio of the biodegradable superabsorbent polymer (Bio-SAP) to the bioadhesive polymer (BP) is 2 to 8:8 to 2.

4. The topical hemostatic powder composition of claim 2, wherein a weight ratio of the biodegradable superabsorbent polymer (Bio-SAP) to the bioadhesive polymer (BP) is 5 to 5.

5. The topical hemostatic powder composition of claim 1, wherein glyoxal is included in an amount of 0.5-2 parts by weight based on 100 parts by weight of the biodegradable superabsorbent polymer (Bio-SAP).

6. The topical hemostatic powder composition of claim 1, wherein a weight ratio of the biodegradable superabsorbent polymer (Bio-SAP) to the bioadhesive polymer (BP) is 2 to 8:8 to 2.

7. A topical hemostatic powder comprising the composition according to claim 1.

8. The topical hemostatic powder of claim 7, wherein an average diameter of the topical hemostatic powder is 1-500 μm.

9. A method for preparing the topical hemostatic powder composition according to claim 1, the method comprising the steps of:

(a) preparing solutions A and B, wherein the solution A is prepared by dissolving chitosan in an aqueous acid solution, and the solution B is prepared by adding sodium starch glycolate to distilled water and dissolving the sodium starch glycolate;

(b) forming the chitosan-sodium starch glycolate semi interpenetrating polymer network (SIPN) structure, by adding glyoxal to a mixed solution in which the solutions A and B are mixed with each other;

(c) preparing the bioadhesive polymer (BP); and (d) mixing the biodegradable superabsorbent polymer (Bio-SAP) with the bioadhesive polymer (BP).

10. The method of claim 9, wherein the solution A in the step (a) comprises 1-20 parts by weight of chitosan based on 100 parts by weight of the aqueous acid solution.

11. The method of claim 9, wherein the solution B in the step (a) comprises 1-10 parts by weight of sodium starch glycolate based on 100 parts by weight of the distilled water.

12. The method of claim 9, wherein the glyoxal is added in an amount of 0.5-2 parts by weight based on 100 parts by weight of the mixed solution in the step (b).

13. The method of claim 9, wherein the bioadhesive polymer (BP) in the step (c) is chitosan chemically modified by thioglycolic acid, which is prepared by using 0.01-4 parts by weight of thioglycolic acid and 1-20 parts by weight of chitosan based on 100 parts by weight of an aqueous acid solution.

14. The method of claim 13, wherein the aqueous acid solution comprises at least one selected from the group consisting of glyoxal, glutaraldehyde, citric acid, 1-ethyl-3 (3-dimethylaminopropyl) carbodiimide (EDAC), N-hydroxysuccinimide (NHS), diisocyanate, and diacetaldehyde as a crosslinking agent.

15. The method of claim 9, wherein, in the step (d) of mixing the biodegradable superabsorbent polymer (Bio-SAP) with the bioadhesive polymer (BP), a mixing weight ratio is 2 to 8:8 to 2.

16. The topical hemostatic powder composition of claim 1, wherein a weight ratio of the biodegradable superabsorbent polymer (Bio-SAP) to the bioadhesive polymer (BP) is 5 to 5.

* * * * *